US010227651B2

(12) United States Patent
Sandrin et al.

(10) Patent No.: US 10,227,651 B2
(45) Date of Patent: Mar. 12, 2019

(54) GENE EXPRESSION BASED BIOMARKER SYSTEM FOR IRRITABLE BOWEL SYNDROME (IBS) DIAGNOSIS

(71) Applicant: ARIZONA BOARD OF REGENTS ON BEHALF OF ARIZONA STATE UNIVERSITY, Scottsdale, AZ (US)

(72) Inventors: Todd Sandrin, Phoenix, AZ (US); Peter Jurutka, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 32 days.

(21) Appl. No.: 15/120,941

(22) PCT Filed: Feb. 24, 2015

(86) PCT No.: PCT/US2015/017331
§ 371 (c)(1),
(2) Date: Aug. 23, 2016

(87) PCT Pub. No.: WO2015/127455
PCT Pub. Date: Aug. 27, 2015

(65) Prior Publication Data
US 2017/0067107 A1    Mar. 9, 2017

Related U.S. Application Data

(60) Provisional application No. 61/943,739, filed on Feb. 24, 2014.

(51) Int. Cl.
*C12Q 1/6883* (2018.01)
(52) U.S. Cl.
CPC ..... *C12Q 1/6883* (2013.01); *C12Q 2600/158* (2013.01)
(58) Field of Classification Search
None
See application file for complete search history.

(56) References Cited

U.S. PATENT DOCUMENTS

2009/0117589 A1    5/2009   Southern
2010/0222228 A1*   9/2010   Thielemans ......... C12Q 1/6883
                                                            506/9
2011/0039869 A1    2/2011   Lee et al.

FOREIGN PATENT DOCUMENTS

WO    2004085677 A2    10/2004
WO    2012158831 A1    11/2012
WO    2015127455 A1     8/2015

OTHER PUBLICATIONS

Whitehead (Genome Biology 2005 vol. 6 Issue 2 Article R13).*
Coleman (Drug Discovery Today. 2003. 8: 233-235).*
Chan (G&P magazine 2006 vol. 6 No. 3 pp. 20-26).*
Aerssens, J. et al., Alterations in mucosal immunity identified in the colon of patients with irritable bowel syndrome., Clin Gastroenterol Hepatol., Feb. 2008, pp. 194-205, vol. 6, No. 2.
Lembo, A. et al., Use of serum biomarkers in a diagnostic test for irritable bowel syndrome, Aliment Pharmacol Ther., Apr. 2009, pp. 834-842, vol. 29, No. 8.
Agreus, L. et al., "Irritable bowel syndrome and dyspepsia in the general population: overlap and lack of stability over time.", Gastroenterology., Sep. 1995, pp. 671-680, vol. 109, No. 3.
Balsari, A. et al., "The fecal microbial population in the irritable bowel syndrome.", Microbiologica., Jul. 1982, pp. 185-194, vol. 5, No. 3.
Barbara, F. et al., "Activated mast cells in proximity to colonic nerves correlate with abdominal pain in irritable bowel syndrome.", Gastroenterology., Mar. 2004, pp. 693-702, vol. 126, No. 3.
Boyce, P. et al., "Irritable bowel syndrome according to varying diagnostic criteria: are the new Rome II criteria unnecessarily restrictive for research and practice?", Am J Gastroenterol., Nov. 2000, pp. 3176-3183, vol. 95, No. 11.
Chadwick, V. et al., "Activation of the mucosal immune system in irritable bowel syndrome.", Gastroenterology., Jun. 2002, pp. 1778-1783, vol. 122, No. 7.
Chey, W. et al., "Utility of the Rome I and Rome II criteria for irritable bowel syndrome in U.S. women", Am J Gastroenterol., Nov. 2002, pp. 2803-2811, vol. 97, No. 11.
Costello, C. et al., "Dissection of the Inflammatory Bowel Disease Transcriptome Using Genome-Wide cDNA Microarrays", PLoS Med., Aug. 2005, pp. 771-778, vol. 2, No. 8, e199.
Dieckgraefe, B. et al., "Analysis of mucosal gene expression in inflammatory bowel disease by parallel oligonucleotide arrays.", Physiol Genomics., Nov. 2000, pp. 1-11, vol. 4, No. 1.
Dooley, T. et al., "Regulation of gene expression in inflammatory bowel disease and correlation with IBD drugs: screening by DNA microarrays.", Inflamm Bowel Dis., Jan. 2004, pp. 1-14, vol. 10, No. 1.
Drossman, D. et al., "U.S. householder survey of functional gastrointestinal disorders. Prevalence sociodemography, and health impact.", Dig Dis Sci., Sep. 1993, pp. 1569-1580, vol. 38, No. 9.
Drossman, D. et al., "Irritable bowel syndrome: a technical review for practice guideline development", Gastroenterology., Jun. 1997, pp. 2120-2137, vol. 112, No. 6.
El-Serag, H., "Impact of irritable bowel syndrome: prevalence and effect on health-related quality of life.", Rev Gastroenterol Disord., 2003, pp. S3-S11, vol. 3, suppl. 2.
Gecse, K. et al., "Fecal serine-protease activity: A possible pathophysiological factor and biomarker for diarrhea-predominant irritable bowel syndrome.", Gastroenterology., Apr. 2007, pp. A83, vol. 132, No. 2, suppl. 2.

(Continued)

*Primary Examiner* — Amanda Haney
(74) *Attorney, Agent, or Firm* — Gavin J. Milczarek Desai; Quarles & Brady LLP

(57) ABSTRACT

We have identified a suite of genes in a limited number of human colonic tissue samples with expression patterns that correlate with whether an individual is experiencing symptoms of Irritable Bowel Syndrome (IBS) (FIG. 2). Interestingly, in the efforts to screen for genes that might be used as biomarkers for IBS, it was found that no single gene could be used for this purpose. Instead, when examining the entire dataset, there exist signature gene expression patterns (e.g., fingerprints or biosignatures) of IBS that have use as a diagnostic tool for IBS.

8 Claims, 10 Drawing Sheets

Specification includes a Sequence Listing.

(56) References Cited

OTHER PUBLICATIONS

Geeraerts, B. et al., "Serotonin transporter gene polymorphisms in irritable bowel syndrome", Neurogasroenterol Motil., Nov. 2006, pp. 957-959, vol. 18, No. 11.
Gonsalkorale, W. et al., "Interleukin 10 genotypes in irritable bowel syndrome: evidence for an inflammatory component?", Gut., Jan. 2003, pp. 91-93, vol. 52, No. 1.
Gwee, K.-W. et al., "Increased rectal mucosal expression of interleukin 1β in recently acquired post-infectious irritable bowel syndrome", Gut., Apr. 2003, pp. 523-526, vol. 52, No. 4.
Hahn, B. et al., "Differences Between Individuals with Self-Reported Irritable Bowel Syndrome (IBS) and IBS-Like Symptoms", Dig Dis Sc., Dec. 1997, pp. 2585-2590, vol. 42, No. 12.
Hammer, J. et al., "Diagnostic criteria for the irritable bowel syndrome.", Am J Med., Nov. 1999, pp. 5S-11S, vol. 107, No. 5A.
Hampe, J. et al., "Association between insertion mutation in NOD2 gene and Crohn's disease in German and British populations.", Lancet, Jun. 2001, pp. 1925-1928, vol. 357, No. 9272.
Hugot, J. et al., "Association of NOD2 leucine-rich repeat variants with susceptibility to Crohn's disease.", Nature, May 2001, pp. 599-602, vol. 411 No. 6837.
Irizarry, R. et al., "Exploration, normalization, and summaries of high density oligonucleotide array probe level data.", Biostatistics, Apr. 2003, pp. 249-264, vol. 4, No. 2.
Kassinen, A. et al., "The fecal microbiota of irritable bowel syndrome patients differs significantly from that of healthy subjects.", Gastroenterology, Jul. 2007, pp. 24-33, vol. 133, No. 1.
Kay, L. et al., "Irritable bowel syndrome: which definitions are consistent?", J Intern Med., Dec. 1998, pp. 489-494, vol. 244, No. 6.
Khalif, I. et al., "Alterations in the colonic flora and intestinal permeability and evidence of immune activation in chronic constipation.", Dig Liver Dis., Nov. 2005, pp. 838-849, vol. 37, No. 11.
Kim, H. et al., "A randomized controlled trial of a probiotic, VSL#3, on gut transit and symptoms in diarrhoea-predominant irritable bowel syndrome.", Aliment Pharmacol Ther., Apr. 2003, pp. 895-904, vol. 17, No. 7.
Kim, H. et al., "Association of distinct α2 adrenoceptor and serotonin transporter polymorphisms with constipation and somatic symptoms in functional gastrointestinal disorders", Gut., Jun. 2004, pp. 829-837, vol. 53, No. 6.
Konikoff, M. et al., "Role of fecal calprotectin as a biomarker of intestinal inflammation in inflammatory bowel disease.", Inflamm Bowel Dis., Jun. 2006, pp. 524-534, vol. 12, No. 6.
Langhorst, J. et al., "Noninvasive markers in the assessment of intestinal inflammation in inflammatory bowel diseases: performance of fecal lactoferrin, calprotectin, and PMN-elastase, CRP, and clinical indices.", Am J Gastroenterol., Jan. 2008, pp. 162-169, vol. 103, No. 1.
Lawrance, I. et al., "Ulcerative colitis and Crohn's disease: distinctive gene expression profiles and navel susceptibility candidate genes.", Hum Mol Genet., Mar. 2001, pp. 445-456, vol. 10, No. 5.
Locke, G. et al., "Natural history of irritable bowel syndrome and durability of the diagnosis.", Rev Gastroenterol Disord., 2003, pp. S12-S17, vol. 3, suppl. 3.
Locke, G. et al., "Gastrointestinal symptoms in families of patients with an SCN5A-encoded cardiac channelopathy: evidence of an intestinal channelopathy.", Am J Gastroenterol., Jun. 2006, pp. 1299-1304, vol. 101, No. 6.
Macsharry, J. et al., "Mucosal cytokine imbalance in irritable bowel syndrome.", Scand J Gastroenterol., 2008, pp. 1467-1476, vol. 43, No. 12.
Malinen, E. et al., "Analysis of the fecal microbiota of irritable bowel syndrome patients and healthy controls with real-time PCR.", Am J Gastroenterol., Feb. 2005, pp. 373-382, vol. 100. No. 2.
Mangin, I. et al., "Molecular inventory of faecal microflora in patients with Crohn's disease.", FEMS Microbiol Ecol., Oct. 2004, pp. 25-36, vol. 50, No. 1.
Mättö, J. et al., "Composition and temporal stability of gastrointestinal microbiota in irritable bowel syndrome—a longitudinal study in IBS and control subjects.", FEMS Immunol Med Microbiol., Feb. 2005, pp. 213-222, vol. 43, No. 2.
Maukonen, J. et al., "Prevalence and temporal stability of selected clostridial groups in irritable bowel syndrome in relation to predominant faecal bacteria.", J Med Microbiol., May 2006, pp. 625-633, vol. 55, pt. 5.
Nikolausz, M. et al., "Observation of bias associated with re-amplification of DNA isolated from denaturing gradient gels.", FEMS Microbiol Lett., Mar. 2005, pp. 385-390, vol. 244, No. 2.
Nobaek, S. et al., "Alteration of intestinal microflora is associated with reduction in abdominal bloating and pain in patients with irritable bowel syndrome.", Am J Gastroenterol., May 2000, pp. 1231-1238, vol. 95, No. 5.
Park, M.I. et al., "Genetics and Genotypes in Irritable Bowel Syndrome: Implications for Diagnosis and Treatment", Gastroenterol Clin N Am., Jun. 2005, pp. 305-317, vol. 34, No. 2.
Meal, K. et al., "Prevalence of gastrointestinal symptoms six months after bacterial gastroenteritis and risk factors for development of the irritable bowel syndrome: postal survey of patients.", BMJ, Mar. 1997, pp. 779-792, vol. 314, No. 7083.
Ogura, Y. et al., "A frameshift mutation in NOD2 associated with susceptibility to Crohn's disease.", Nature, May 2001, pp. 603-606, vol. 411, No. 6837.
Ohman, L. et al., "A Controlled Study of Colonic Immune Activity and β7+ Blood T Lymphocytes in Patients With Irritable Bowel Syndrome", Clin Gastroenterol Hepatol., Oct. 2005, pp. 980-986, vol. 3, No. 10.
O'Mahony, L. et al., "Lactobacillus and bifidobacterium in irritable bowel syndrome: a symptom responses and relationship to cytokine profiles.", Gastroenterology., Mar. 2005, pp. 541-551, vol. 128, No. 3.
Pata, C. et al., "Association of the -1438 G/A and 102 T/C polymorphism of the 5-Ht2A receptor gene with irritable bowel syndrome 5-Ht2A gene polymorphism in irritable bowel syndrome.", J Clin Gastroenterol., Aug. 2004, pp. 561-566, vol. 38, No. 7.
Poullis, A. et al., "Review article: Faecal markers in the assessment of activity in inflammatory bowel disease.", Ailment Pharmacol Ther., Apr. 2002, pp. 675-681, vol. 16, No. 4.
Ringel, Y. et al., "Irritable Bowel Syndrome.", Annu Rev Med., 2001, pp. 319-338, vol. 52.
Saito, Y. et al., "A comparison of the Rome and Manning criteria for case identification in epidemiological investigations of irritable bowel syndrome.", Am J Gastroenterol., Oct. 2000, pp. 2816-2824, vol. 95, No. 10.
Saito, Y. et al., "The epidemiology of irritable bowel syndrome in North America: a systematic review.", Am J Gastroenterol., Aug. 2002, pp. 1910-1915, vol. 97, No. 8.
Saito, Y. et al., "Association of the 1438G/A and 102T/C polymorphism of the 5-HT2A receptor gene with irritable bowel syndrome 5-HT2A gene polymorphism in irritable bowel syndrome.", J Clin Gastroenterol., Oct. 2005, pp. 835, vol. 39, No. 9.
Siegrist, T. et al., "Discrimination and characterization of environmental strains of *Escherichia coli* by matrix-assisted laser desorption/ionization time-of-flight mass spectrometry (MALDI-TOF-MS).", J Microbiol Methods., Mar. 2007, pp. 554-562, vol. 68, No. 3.
Spiller, R., "Potential future therapies for Irritable Bowel Syndrome: Will Disease Modifying Therapy as Opposed to Symptomatic Control Become a Reality?", Gastroenterol Clin N Am., Jun. 2005, pp. 337-354, vol. 34, No. 2.
Spiller, R., "Increased rectal mucosal enteroendocrine cells, T lymphocytes, and increased gut permeability following acute Campylobacter enteritis and in post-dysenteric irritable bowel syndrome.", Gut., Dec. 2000, pp. 804-811, vol. 47, No. 6.
Talley, N. et al., "Diagnostic value of the Manning criteria in irritable bowel syndrome.", Gut., Jan. 1990, pp. 77-81, vol. 31, No. 1.
Talley, N., "Diagnosing an irritable bowel: Does sex matter?", Gastroenterology, 1991, pp. 835-837, vol. 100, No. 3.
Talley, N. et al., "Onset and disappearance of gastrointestinal symptoms and functional gastrointestinal disorders.", Am J Epidemiol., Jul. 1992, pp. 165-177, vol. 136, No. 2.

(56) References Cited

OTHER PUBLICATIONS

Talley, N., "Environmental versus genetic risk factors for irritable bowel syndrome: clinical and therapeutic implications.", Rev Gastroenterol Disord., 2005, pp. 82-88, vol. 5, No. 2.

Talley, N., "Functional Gastrointestinal Disorders in 2007 and Rome III: Something New, Something Borrowed, Something Objective.", Rev Gastroenterol Disord., 2007, pp. 97-105, vol. 7, No. 2.

Thompson, W. et al., "Functional bowel disorders and functional abdominal pain.", Gut., 1999, pp. II43-II47, vol. 45, suppl. 2.

Törnblom, H. et al., "Full-Thickness Biopsy of the Jejunum Reveals Inflammation and Enteric Neuropathy in Irritable Bowel Syndrome.", Gastroenterology, Dec. 2002, pp. 1972-1979, vol. 123, No. 6.

Van Der Veek, P. et al., "Role of tumor necrosis factor-alpha and interleukin-10 gene polymorphisms in irritable bowel syndrome.", Am J Gastroenterol., Nov. 2005, pp. 2510-2516, vol. 100, No. 11.

Van Kerkhoven, L. et al., "Meta-analysis: a functional polymorphism in the gene encoding for activity of the serotonin transporter protein is not associated with the irritable bowel syndrome.", Ailment Pharmacol Ther., Oct. 2007, pp. 979-986, vol. 26, No. 7.

Vanner, S. et al., "Predictive value of the rome criteria for diagnosing the irritable bowel syndrome.", Am J Gastroenterol., Oct. 1999, pp. 2912-2917, vol. 94, No. 10.

Verdu, E., et al., "Irritable bowel syndrome.", Best Pract Res Clin Gastroenterol., 2004, pp. 315-321, vol. 18, No. 2.

Von Stein, P. et al., "Multigene Analysis Can Discriminate Between Ulcerative Colitis, Crohn's Disease, and Irritable Bowel Syndrome.", Gastroenterology., Jun. 2008, pp. 1869-1881, vol. 134, No. 7.

Wu, F. et al., "MicroRNAs Are Differentially Expressed in Ulcerative Colitis and Alter Expression of Macrophage Inflammatory Peptide-2α.", Gastroenterology, Nov. 2008, pp. 1624-1635, vol. 135, No. 5.

Zuckerman, S. et al., "Effect of surface-adsorbed proteins and phosphorylation inhibitor AG18 on intracellular protein expression in adherent macrophages.", Biomaterials., Jul. 2006, pp. 3745-3757, vol. 27, No. 20.

Yale, S. et al., "Applying Case Definition Criteria to Irritable Bowel Syndrome.", Clin Med Res., May 2008, pp. 9-16, vol. 6, No. 1.

Patent Cooperation Treaty, International Preliminary Report on Patentability and Written Opinion for PCT/US2015/017331, International Searching Authority, 7 pages, dated May 22, 2015.

Patent Cooperation Treaty, International Search Report for PCT/US2015/017331, International Searching Authority, 3 pages, dated May 22, 2015.

Prometheus Therapeutics & Diagnostics, "Promethus IBD sgi Diagnostic (Brochure)", Nestlé Health Science, 2013.

Roche Nimblegen, Inc., "NimbleGen Gene Expression Microarrays and Services: High-density arrays for sensitive and accurate genome-wide gene expression profiling", Roche, 2008.

* cited by examiner

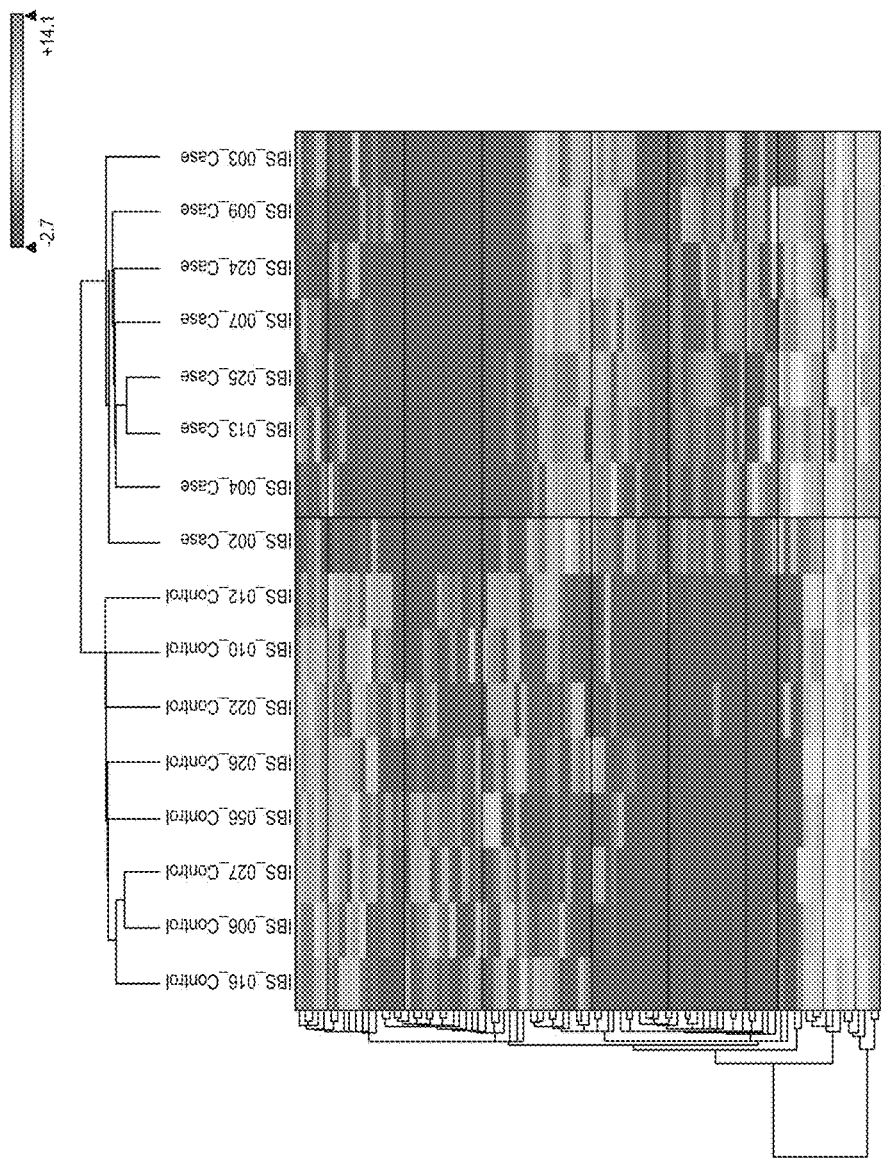

Validating the Array Data: qPCR results

| GENE NAME | GENE CHIP | Repeat #1 | CONCLUSIONS | RELATIVE TO GENE CHIP |
|---|---|---|---|---|
| TRIP13 | 5.1 up | 1.845 up | DOWN | Not Confirmed |
| TDRD6 | 8.1 up | 0.792 down | UP | Confirmed |
| KRTAP16-1 | 5.3 down | 0.282 down | DOWN | Confirmed |
| ADORA1 | 5.6 down | 1.506 up | UP | Not Confirmed |
| SNX10 | 5.8 down | 0.667 down | DOWN | Confirmed |
| EPHA3 | 5.3 down | 0.387 down | DOWN | Confirmed |
| ZDHHC15 | 10.7 up | 0.266 down | DOWN | Not Confirmed |
| MBD2 | 5.9 down | 1.818 up | UP | Not Confirmed |
| FLT4 | 7.7 up | 2.382 up | UP | Confirmed |
| MSR1 | 5.1 down | 0.884 down | UP | Not Confirmed |

| CASE Subject | | | |
|---|---|---|---|
| Visit | 1 | 2 | 3 (Unscheduled) |
| Week | 0 | | (Unscheduled) |
| Window (Days) | | | |
| Eligibility | X | | |
| Informed consent | X | | |
| Medical History | X | | |
| Family History | X | | |
| Francis Severity IBS Questionnaire | X | | X |
| IBS-QOL | X | | X |
| Blood | X | | |
| CBC w/o diff | | | |
| Comprehensive Metabolic Panel | | | |
| Quantitative Serum Immunoglobin-IgM only | | | |
| Gasar Tissue Transglutaminase-AB, IGA, | | | |
| Stool Sample | X | | X |
| Colonoscopy | | X | |
| Tissue Biopsies | | X | |

FIG. 10A

| CONTROL Subject | | |
|---|---|---|
| Visit | 1 | 2 |
| Week | 0 | |
| Eligibility Screening Informed consent | X | |
| Medical History Family History | X | |
| Blood | X | |
| CBC w/o diff | X | |
| Comprehensive Metabolic Panel | X | |
| Quantitative Serum Immunoglobin-IgM only | | |
| Gasar Tissue Transglutaminase-AB, IGA, IGG | | |
| ESR | | |
| Stool Sample | X | |
| Colonoscopy | | X |
| Tissue Biopsies | | X |

FIG. 10B

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctcctacggg aggcagcagt                    20

<210> SEQ ID NO 2
<211> LENGTH: 18
<212> TYPE: DNA
<213> ORGANISM: artificial sequence
<220> FEATURE:
<223> OTHER INFORMATION: Primer

<400> SEQUENCE: 2
gcggtgtgta caagrccc                      18

GENE EXPRESSION BASED BIOMARKER SYSTEM FOR IRRITABLE BOWEL SYNDROME (IBS) DIAGNOSIS

CROSS-REFERENCE TO RELATED APPLICATIONS

This application is a 371 application of PCT/US2015/017331 filed Feb. 24, 2015, which claims priority to U.S. Provisional Patent Application No. 61/943,739 filed on Feb. 24, 2014.

BACKGROUND OF THE INVENTION

Approximately 9% of the general population will report the onset of IBS over a 1 year period. Despite this, no standard and reliable diagnostic test for IBS is currently available. As such, there is keen interest in development of a rapid and accurate diagnostic test for IBS.

IBS is a functional disorder of the gastrointestinal tract characterized by abdominal pain or discomfort along with changes in the frequency or consistency of the stool. IBS most commonly occurs during the third and fourth decade of life, with decreasing incidence rates in the sixth and seventh decade. Symptoms of IBS are a common reason that patients seek medical care from gastrointestinal specialists and account for 2.4-3.5 million physician visits annually. Since there are no structural abnormalities or biochemical markers associated with IBS, the diagnosis is based on the presence of clinical symptoms using specific, validated criteria.

Symptom-based consensus-derived diagnostic criteria have been established to create uniformity in reporting and to enhance diagnostic accuracy. The criteria used to establish the diagnosis of IBS have evolved reflecting a better understanding of the symptomatology associated with this disease. The newer and the most recent criteria reflect more specific clinical diagnostic standards such that many patients previously diagnosed with IBS, may have been mislabeled and hence misdiagnosed based on the latest criteria. Conversely, more restrictive case definitions of the criteria may lead to patients being under diagnosed with IBS. Another limitation of the diagnostic criteria is that they do not account for differences in disease severity or differences among distinct pathophysiologic subgroups. Furthermore, symptoms experienced by patients with IBS often overlap with other gastrointestinal disease which creates considerable uncertainty among physicians and concerns about potentially missing other gastrointestinal diseases.

Approximately 9% of the general population will report the onset of IBS over a 1 year period. Despite this, no standard and reliable diagnostic test for IBS is currently available. As such, there is keen interest in development of a rapid and accurate diagnostic test for IBS. Therefore, improvements in methods and systems for accurate identification of individuals with a genetic predisposition for developing IBS are desirable.

SUMMARY OF THE INVENTION

The embodiments described herein relate to methods and a devices for identifying a gene expression pattern associated with irritable bowel syndrome within a patient gene profile. Furthermore, methods of diagnosis for IBS are described.

In one aspect, certain embodiments relate to a method of screening a genetic profile for genes associated with IBS including providing a patient genetic profile including a patient gene expression pattern, providing a control genetic profile including a control gene expression pattern, and comparing the patient gene expression pattern to the control gene expression pattern to identify a substantial presence of a gene expression pattern associated with a health disorder in the patient gene expression pattern.

In one aspect, certain embodiments relate to a device for identifying an association of genes with irritable bowel syndrome including a statistical analyzer, a control image of a microarray of control cDNA hybridized to DNA submitted to the statistical analyzer, a patient image of a microarray of patient cDNA hybridized to DNA submitted to the statistical analyzer, and a statistical analysis provided by the statistical analyzer in response to the submission of the control image and the patient image, wherein the statistical analysis identifies whether a gene expression pattern associated with irritable bowel syndrome is substantially present in the patient image as compared to the control image.

We have identified a suite of genes in a limited number of human colonic tissue samples with expression patterns that correlate with whether an individual is experiencing symptoms of Irritable Bowel Syndrome (IBS). Interestingly, in our efforts to screen for genes that might be used as biomarkers for IBS, we found no single gene that could be used for this purpose. Instead, when examining the entire dataset, we noticed signature gene expression patterns (e.g., fingerprints or biosignatures) of IBS that can be marketed as a diagnostic tool for IBS.

These and other aspects of the invention will be apparent upon reference to the following detailed description and figures. To that end, any patent and other documents cited herein are hereby incorporated by reference in their entirety.

BRIEF DESCRIPTION OF THE DRAWINGS

FIG. 8 illustrates a representation of two-way cluster analysis diagrams in which expression of an individual gene is shown as a rectangle in a color denoting expression level (blue=gene is down regulated in IBS patients relative to controls; red=gene is up regulated in IBS patients relative to controls). The representation contains genes differentially expressed by a factor of 2 or more, according to an embodiment. The genes are first clustered horizontally (in rows) then clustered vertically.

FIG. 9A illustrates quantitative PCR (qPCR) results used to validate and characterize differential expression of 10 candidate biomarker genes.

FIG. 9B depicts total RNA isolation amounts for IBS case and control samples.

FIGS. 10A and 10B illustrate IBS case and control subject Schedule of Measurements and criteria assessed for study.

Figure 1:
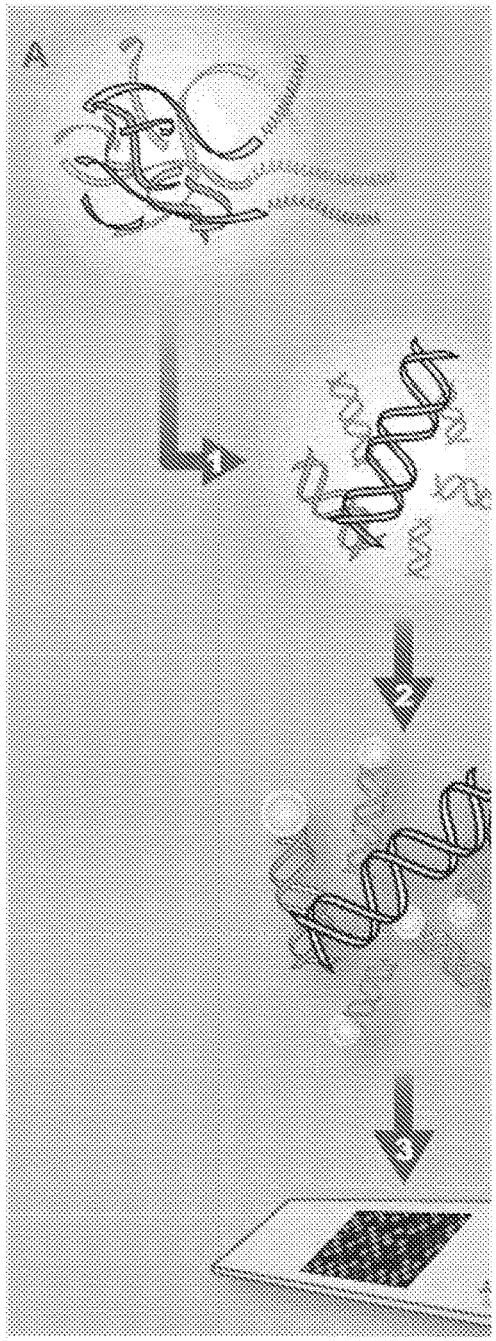
FIG. 1 illustrates a schematic of a microarray approach to identification of differentially expressed genes. RNA (top) is reverse transcribed to a more stable form, cDNA (following arrow 1), fluorescently labeled for detection (following arrow 2), and hybridized to a microarray containing multiple copies of each gene in the genome (following arrow 3). The microarrays we use contain 385,000 features that represent 47,633 genes in the human genome. In this approach, a separate microarray is used for each patient sample.
Figure 2:
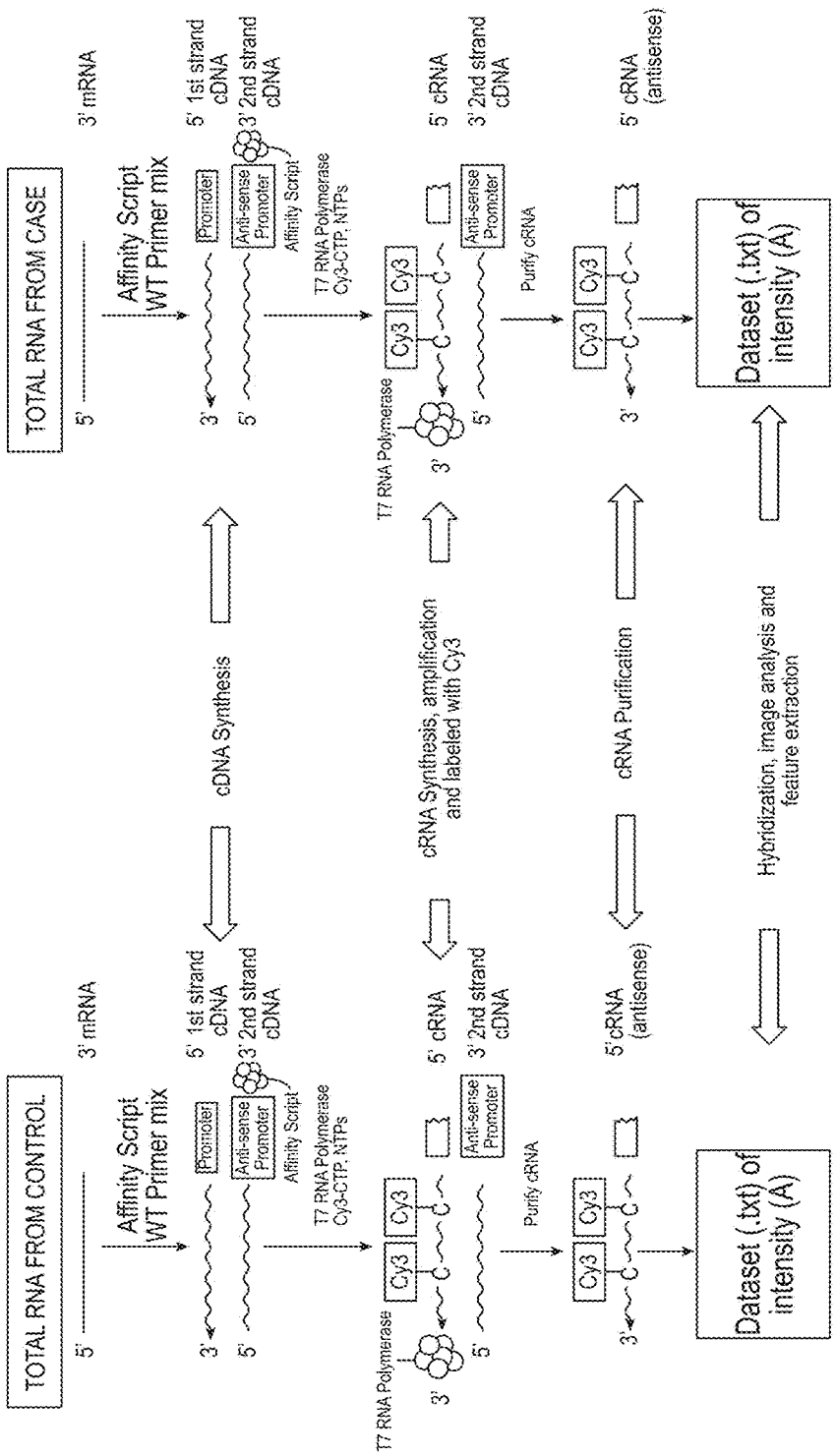
FIG. 2 illustrates a schematic of a working example of preparation of patient cDNA hybridized to human genome DNA to form a patient microarray. Also shown is preparation of control cDNA hybridized to human genome DNA to form a control microarray, according to an embodiment.
Figure 3:
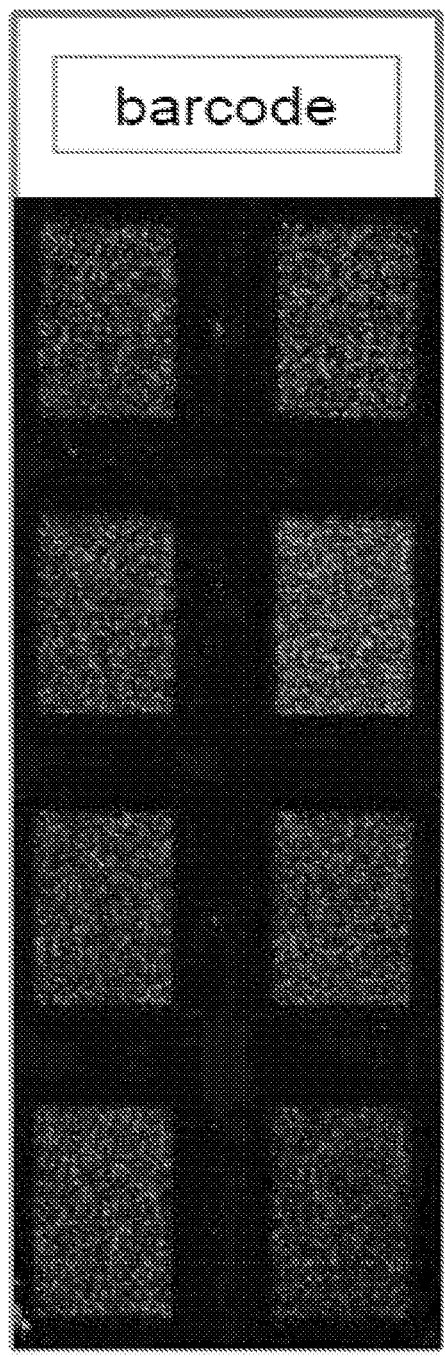
FIG. 3 illustrates a SurePrint G3 Human GE v2 8× 60K microarray, according to an embodiment.
Figure 4:
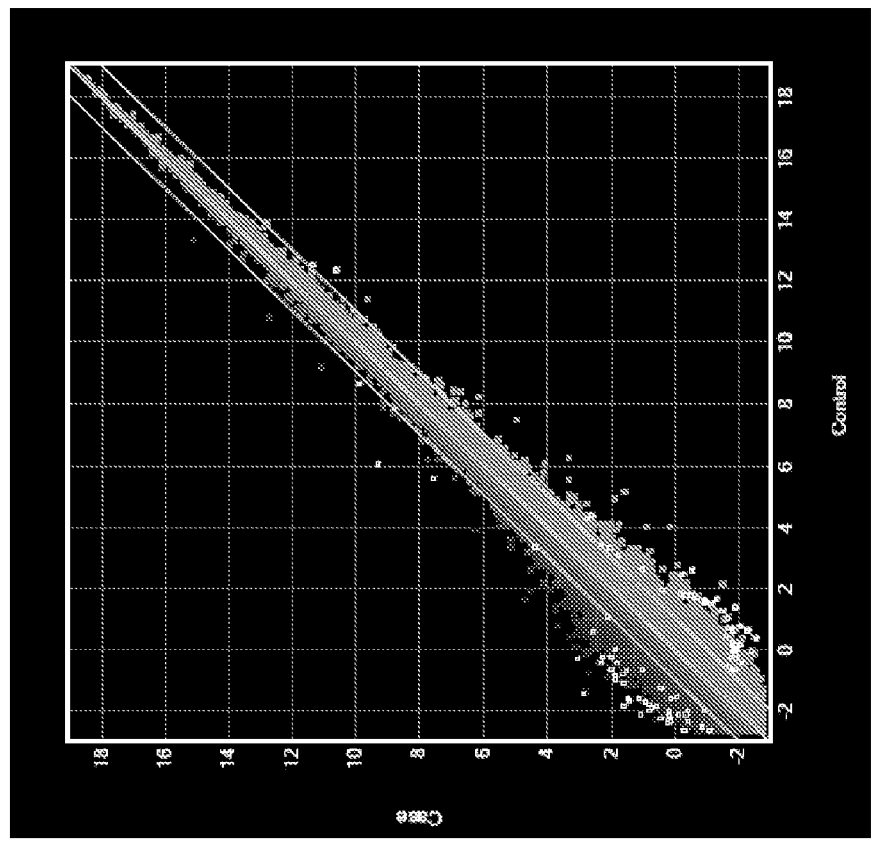
FIG. 4 illustrates fluorescent data indicating 92 genes at 2-fold change and 99% confidence, 55 genes at 44-fold change and 99% confidence, and 9 genes at 8-fold change and 99% confidence, according to an embodiment.
Figure 5:
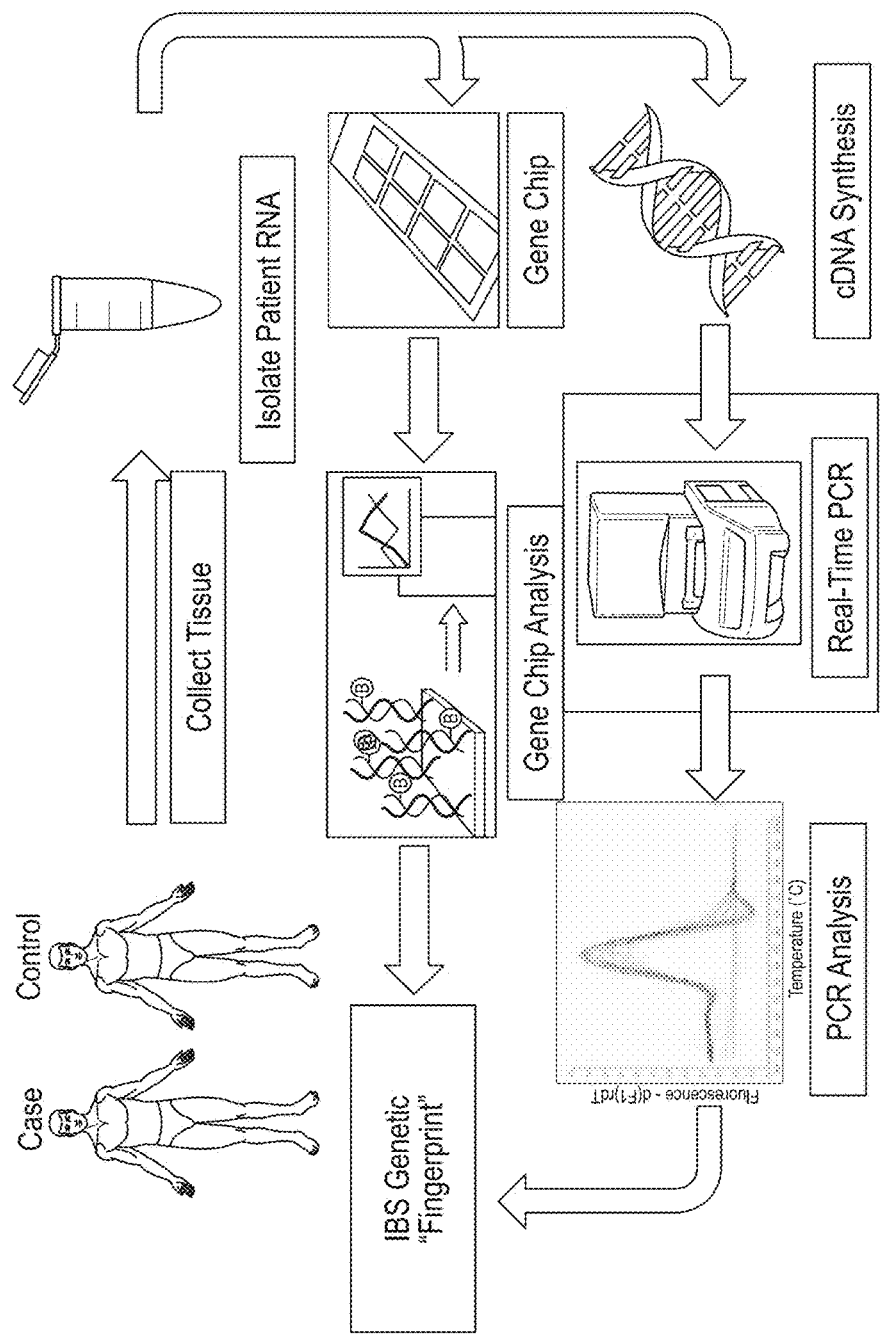
FIG. 5 illustrates a schematic validating the microarray results from FIG. 3 using qPCR, according to an embodiment.
Figure 6:
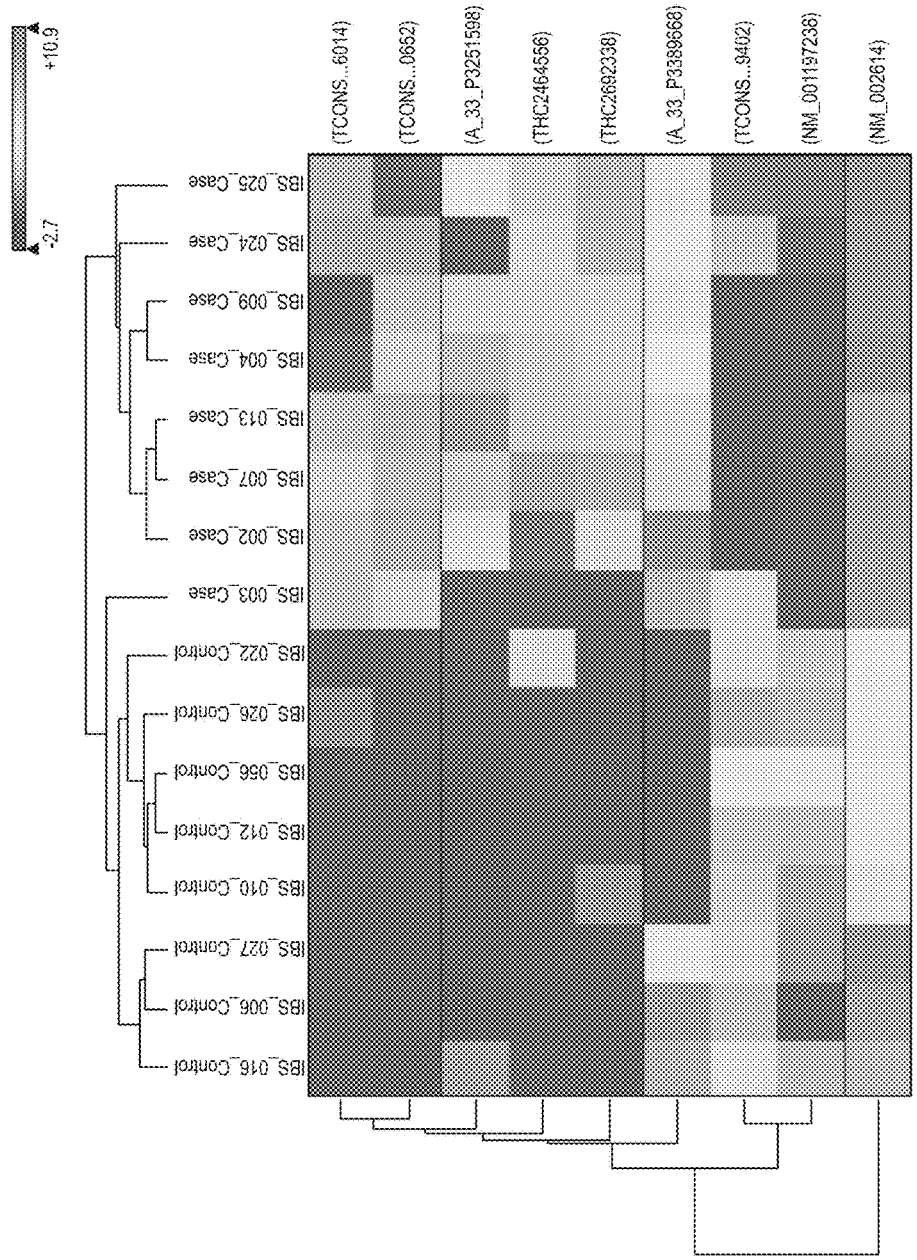
FIG. 6 illustrates a representation of two-way cluster analysis diagrams in which expression of an individual gene is shown as a rectangle in a color denoting expression level (blue=gene is down regulated in IBS patients relative to controls; red=gene is up regulated in IBS patients relative to controls). The representation contains all genes differentially expressed by a factor of 8 or more, according to an embodiment.
Figure 7:
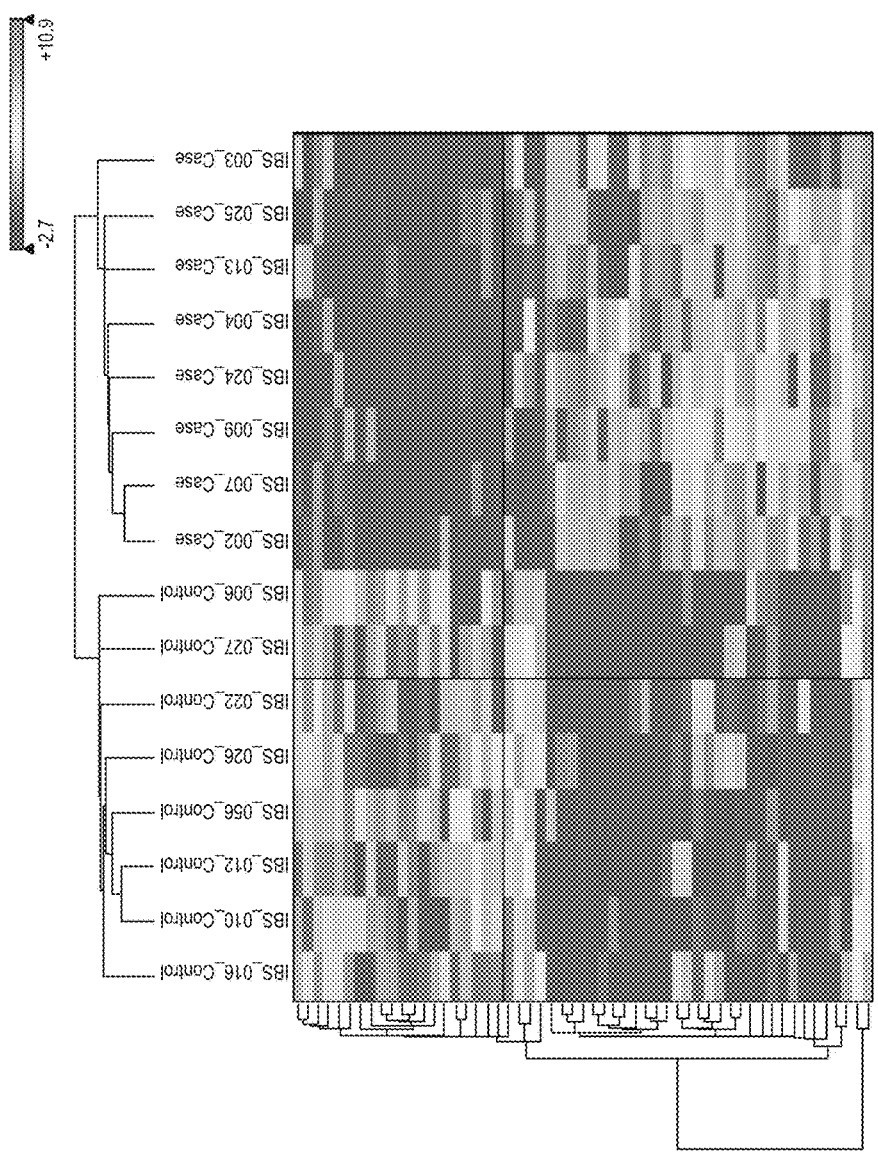
FIG. 7 illustrates a representation of two-way cluster analysis diagrams in which expression of an individual gene is shown as a rectangle in a color denoting expression level (blue=gene is down regulated in IBS patients relative to controls; red=gene is up regulated in IBS patients relative to controls). The representation contains all genes differentially expressed by a factor of 4 or more, according to an embodiment.

What is striking in all of these figures is that cases and controls tend to group together, suggesting that expression of suites of genes (or expression patterns/fingerprints) might be collected, stored in a library/database, then used to identify whether an individual has IBS or not.

DETAILED DESCRIPTION OF THE INVENTION

Embodiments described herein relate to diagnostic methods, specifically to a methods and systems of determining patients with IBS due to their unique gene expression patterns compared to healthy control patients.

The diagnosis of irritable bowel syndrome (IBS) is currently based on symptomatic criteria that exclude other conditions affecting the gastrointestinal tract, such as celiac disease, food allergies, and infections. The absence of appropriate diagnostic and therapeutic approaches for IBS places a significant burden on the patient and the health care system due to direct and indirect costs of care. Limitations associated with the application of symptomatic criteria include inappropriate use and/or intrinsic limitations such as the population to which these criteria are applied. The lack of biomarkers specific for IBS, non-specific abdominal symptoms, and considerable variability in the disease course creates additional uncertainty during diagnosis. We have developed screening methods of tissue samples from patients with verified IBS to identify gene expression-based biomarkers associated with IBS.

DNA microarrays allow rapid screening of entire genomes for genetic biomarkers and are, thus a more logical technology with which to embark upon a search for IBS biomarkers. For this reason, we employ ultra-high density microarrays to examine samples for the presence of candidate biomarkers. Identification and validation of such biomarkers leads to a better understanding of the etiology of IBS, and now to a new diagnostic test for IBS.

Emerging evidence suggests that IBS is a complex disease marked by different pathogenetic and pathophysiologic interacting factors. Although we have initially evaluated gene expression profiling using DNA microarrays on intestinal mucosal tissue samples, we now collected fecal and blood samples for the evaluation of protein biomarkers and bacterial candidate(s) involved in IBS. This is particularly important given the complex interaction of environmental, intestinal microbiota and local and systemic immunologic factors involved in disease pathogenesis. Procurement of fecal, blood and tissue samples simultaneously assists us in better understanding the complex interaction and relationship of genes, protein expression and intestinal microbiota in symptomatic patients with IBS.

This is a multi-site study where subjects were recruited and enrolled at 4 sites (University of Wisconsin-Madison, Gundersen Lutheran Medical Center, La Crosse, Wis. and Marshfield Clinic/Marshfield Clinic Research Foundation, Marshfield, Wis.) conducted through the Wisconsin Network for Health Research (WiNHR), a collaboration of health services researchers across the state of Wisconsin working to improve the health of Wisconsin.

The aim of this study was to determine if patients with IBS have unique gene expression patterns compared to healthy control patients. The study was conducted in 2 phases:

Phase I

Indentifying differentially expressed genes in patients with IBS which were developed into accurate and rapid biomarkers for IBS to ensure consistent implementation of this study across all study sites.

Phase II*

For Phase II initiatives, we searched for unique and/or differentially expressed proteins in stool and serum samples using mass spectrometry (MALDI-TOF and LC/MS). Additional work included evaluation of microbial biomarkers, which involves construction of and examination of clone libraries during symptomatic (active disease) and asymptomatic periods to determine whether particular intestinal microorganisms are present and/or more or less abundant in symptomatic patient stool samples.

*Collection of additional samples (blood and stool) at the same time as the tissue sample collection (Phase I) provides composite information about potential interactions between the intestinal microbiome and expression of other blood biomarkers in IBS patients during periods of active disease and during an asymptomatic period.

A. Incidence of IBS

Incidence estimates are derived primarily from multiple surveys over time. Incidence data are difficult to obtain due to a number of factors including: the fluctuating nature of the disease, differing case definitions, a lack of natural history studies, and uncertainty of whether symptoms were present prior to surveying. Incidence data derived from patient office visits has been reported to range from 196 to 250 cases per 100,000 person-years. We reported a similar crude incidence rate in the MESA population of 128 to 250 cases per 100,000 person-years (CI lower 93-199, upper 163-302) for odd numbered years between 1993 and 2003 based on symptomology documented in the medical record with lower rates based on specific diagnostic criteria of IBS. Population-based surveys report that approximately 9% of the general population will report the onset of IBS symptoms over a 1-year period. When persons with any previous symptoms are excluded, the true incidence is probably 1-2%.

B. Diagnosis

The Rome criteria were developed to create uniformity of reporting and to allow comparisons among population subgroups in diagnostic and therapeutic trials as well as epidemiological IBS studies. These criteria were developed and refined by a consensus group of experts in Rome, Italy in order to improve the predictive value of the diagnosis of IBS. The Rome criteria differed from the Manning criteria by specifying that symptoms must be continuous or recurrent (symptom duration), by including abdominal bloating and distention and constipation-type symptoms, and requiring two or more patterns of defecation. The more recent criteria, the Rome II criteria emphasized the importance of pain in the diagnosis of IBS. Rome III criteria are essentially unchanged compared to the Rome II criteria. Rome II is distinguished from Rome I by requiring abdominal pain and altered bowel disturbances for diagnosis, excluding the duplication of items regarding stool frequency and consistency and specifying duration of abdominal pain and other symptoms. The Rome II requires that two of the three main diagnostic criteria be present for diagnosis. There are a number of potential limitations of the Rome II criteria including (1) the requirements for abdominal pain, (2) failure to define the type of pain or discomfort experienced, (3) duration of symptoms for at least 12 weeks and, (4) absence of a requirement for postprandial pain or urgency.

C. Pathophysiology of IBS

Current understanding of the pathophysiology of IBS suggests a complex and heterogeneous disorder in which environmental, visceral perception, gastrointestinal motility, intestinal microbiota, and immunological factors may be involved in disease pathogenesis. It is becoming increasingly recognized that there are categories of IBS differentiated by their pathophysiologic presentation. For example, a post-infectious type of IBS is believed to account for at least 10% of IBS cases. A variety of bacterial and viral (norovirus) pathogens have been reported to account for this condition. The risk of post-infectious IBS appears to be independent of the bacterial pathogen initially causing symptoms of acute gastroenteritis. This suggests that in some patients a common pathway triggered by environmental pathogens in a genetically susceptible host may lead to an inflammatory trigger and post-infectious IBS. Low-grade inflammation and evidence for immune activation has been described in a subset of patients with both diarrhea and constipation subtypes of post-infectious and non-specific IBS. Evidence for immune activation has been demonstrated by the finding of increased CD3+ lymphocytes and enhanced expression of mucosal proinflammatory cytokine interleukin (IL)-1β mRNA in patients with IBS. A consistently recognized feature of IBS is the finding of an increased number of mast cells in close proximity to nerves of the colonic mucosa with a numeric correlation to pain perception.

Additional evidence for the role of inflammation was the finding of a lower concentration of Il-10/Il-12 ratio in some patients with IBS and normalization of this ratio when treated with probiotics. In some patients, low IL-10 levels may be due to genetic differences leading to impaired downregulation of the inflammatory response. The inconsistency among reports in identifying intestinal inflammation and mediators may reflect the variations among populations studied, incomplete documentation of infectious etiologies, or variations among the site of colon biopsy. A causal relationship between the low-grade inflammatory changes and symptoms of IBS has not been firmly established.

D. Genetic Factors

Twin and family studies suggest that there is a genetic basis for IBS. Several candidate genes have been suggested to be involved in the pathogenesis of IBS. One of these genes, serotonin transporter protein or SERT has a gene-linked polymorphic region (SERT-P) that modulates SERT gene transcription and serotonin reuptake in the presynaptic cleft. The SERT gene is characterized by a long (l) and short (s) arm, and the homozygous short (s/s) and heterozygous (l/s) polymorphism is suggested in some populations to be associated with the diarrhea subtype of IBS. The heterogeneous distribution of SERT-P can be accounted for by differences in the prevalence, ethnicity, patient selection, and sample size of the population studied. A recent meta-analysis showed an inconsistency among the association of SERT promoter polymorphisms and IBS in general or subtypes of IBS. IL-10 an anti-inflammatory cytokine is another gene believed to be important in downregulating the inflammatory response. High producing genotypes (G/G) are less commonly found in selected patients with IBS compared to controls. Other genes associated with IBS include polymorphisms of α2 adrencoreceptor polymorphism, 5HT2a receptor and SCN5A channelopathy mutation.

The major challenge with gene association studies has been the failure to replicate findings. An inability to replicate findings can be attributed to a number of factors including, among others, small sample sizes, racial homogeneity of control and disease groups, and ethnicity differences among the populations studied.

E. Current State of the Search for Genetic Biomarkers of IBS

Rather recent technological advances in molecular biology have allowed rapid, genome-wide searches for biomarkers for gastroenterological disorders. The completion of human genome sequencing has enabled high-throughput, whole genome-scale approaches to identifying genes important in the pathophysiology of disease. Typically, oligonucleotides representing all genes are arranged on a glass slide called a microarray (see FIG. 1).

Patient DNA or RNA is applied to the array to determine: 1) whether a particular gene (DNA) is associated with disease susceptibility or 2) whether genes within patients are differentially expressed (RNA).

While straightforward, the search for merely the presence or absence of particular susceptibility gene forms is less likely to rapidly identify useful biomarkers than a search for differential expression of particular genes. With IBD, searches for disease susceptibility genes (not their expression patterns) have revealed several genes associated with the disease including variations in the NOD2/CARD15 gene on chromosome 16. This underscores the enormous complexity and polygenic risk factors that likely exist between different patients. In addition, all individuals with particular disease susceptibility genes may not exhibit similar symptoms. In contrast, biomarkers based on gene expression should allow conclusive diagnosis of IBS through identification of both the presence and activity of IBS-associated genes.

As a result of the promising, high-throughput nature of microarrays, studies have used microarray technology to explore IBD, CD, ulcerative colitis (UC), and IBS. Microarrays were first employed to study mucosal gene expression in the tissue of patients with IBD. The study resulted in investigation of gene expression in patients with UC as well as inflamed and noninflamed controls. Several gene transcripts involved in the inflammatory response characteristic of active UC were identified. As such, the study served as a proof-of-concept for using microarray-based gene expression analyses in larger populations. In another study microarrays were used to more clearly elucidate the pathophysiologies of IBD, UC, and CD. With UC samples, researchers detected differential expression of many genes not previously associated with the disorder including novel genes involved in the immune response (e.g., IGHG3, CD74) and cancer-related processes (e.g., DD96, DRAL). UC and CD were readily distinguished by this approach in that 170 genes were differentially regulated in each disorder.

Results from these studies underscore the power of microarrays to rapidly discover genes associated with gastroenterological disorders. While results from each of these studies are illuminating, it is important to note that the microarrays employed in previous studies contained less probes than the high density arrays we propose to use which contain 9,000 more genes than conventionally used. Thus, our use of high density microarrays has the potential to identify far more differentially expressed genes and candidate biomarker genes than previous studies.

Identification of gene expression profiles at a genome-wide level in symptomatic patients with IBS using cDNA microarrays.

Rationale for the Selection of Outcome Measures

Recent work conducted at our institution sought to identify and validate cases of IBS based on Manning, Rome I and Rome II diagnostic criteria during odd numbered years from 1993-2003 for patients seeking medical care at the Marshfield Clinic and residing in MESA. Incident IBS diagnoses were identified in 890 cases. Symptoms met case definitions for IBS based on at least one diagnostic criterion in 404 patients, 340 (84%) met the Manning criteria, 35 (10%) met Manning and Rome I criteria, 4 (1%) met Manning and Rome II criteria, and 25 (6%) met Manning and Rome I and Rome II criteria. We found that only a small percentage of IBS cases with assigned diagnostic codes met case definition criteria for IBS. There were low concordance rates among the three diagnostic criteria applied. We postulated that the lack of a standard definition in the absence of tissue or other biologic markers impeded the ability to make accurate diagnoses.

In the retrospective study described above the quality of medical record documentation for clinical symptoms of IBS was determined, and IBS diagnoses were validated based on the Manning, Rome I and Rome II criteria. We found that the physicians do not use, ask or specifically record symptoms based on established diagnostic criteria. Furthermore, the Rome criteria are limited in that they were established for research and epidemiological purposes and not clinical practice settings. The results from this study could not be extrapolated and were not transferrable to the current project. Thus, we applied the Rome III criteria.

Working Example 1

Overview or Design Summary

To address the need for identifying IBS specific genetic biomarkers, we proposed screening 16 tissue samples obtained by endoscopy from patients with a verified symptomatic new or verified symptomatic prior diagnosis of IBS (diarrhea and mixed variant) made at the Marshfield Center, Marshfield, University of Wisconsin-Madison, and Gundersen Lutheran Medical Center, La Crosse, Wis. by a gastroenterologist. A total of 16 patients (8 cases and 8 controls) were enrolled.

Age and gender-matched controls (8) were selected based on absence of gastrointestinal symptoms, family or personal history of colon polyps or colon cancer scheduled to undergo colonoscopy for routine colon cancer surveillance with endoscopic and histological examination yielding no significant pathological findings. We enrolled cases 45-60 years of age and controls 50-65 years of age, matching case/controls within ±5 years.

Subject Selection and Withdrawal

IBS Patient Inclusion Criteria (IBS Patient Cases)
1. Clinical diagnosis of IBS compatible with the Rome III criteria with symptoms of abdominal pain or discomfort (uncomfortable sensation not described as pain) at least 3 days/month in the last 3 months associated with 2 or more of following features: (1) improvement with defecation, (2) onset associated with a change in frequency of the stool, (3) onset associated with a change in form (appearance of stool).
2. Diarrhea-predominant subtype of IBS (IBS-D) characterized by loose (mushy) or watery stools** on at least 25% of the bowel movements and hard or lumpy stool* <25% of bowel movements, or Mixed subtype of IBS with the presence of both hard or lumpy stools* and loose (mushy) or watery stools** occurring, in each case, on at least 25% of the bowel movements.
3. Initial diagnosis of IBS confirmed by a gastroenterologist.
4. Males or females 45-60 years of age.
5. IBS symptoms present at the time of enrollment.
6. Recommendation by a gastroenterologist and scheduled to undergo colonoscopic examination.
7. Collection of written informed consent.
* Bristol Stool Form Scale 1-2
** Bristol Stool Form Scale Healthy Patient Inclusion Criteria (Controls)
1. Male or female 50-65 years of age undergoing colon cancer surveillance with endoscopic and histological examination yielding no significant pathological findings.
2. Collection of written informed consent.

Exclusion Criteria (Case and Controls)
1. Participants were not able to understand or provide written informed consent.
2. The research team deemed that the participant may not be able to follow the study protocol.
3. Coexisting organic gastrointestinal diseases (e.g. Crohn's disease, ulcerative colitis, celac disease, active gallstones, diverticulitis and chronic pancreatitis). Diverticula or incidental internal hemorrhoids were not considered a basis for exclusion.
4. Pregnancy
5. Lactose intolerance (based on self-report) or immunodeficiency.
6. Antimicrobials or corticosteroids use in the previous month.
7. On probiotics and were not willing to discontinue this medication for at least 2 weeks prior to enrollment
8. Previous major abdominal surgery with the exception of abdominal wall hernia repair, appendectomy, caesarian section, tubal ligation, laparoscopic cholocystectomy, hysterectomy.
9. Alarming or "red flag" symptoms (e.g. rectal bleeding, anemia, weight loss, persistent fever, etc).
10. History of inflammatory bowel disease (IBD).
11. Recent (3 month) travel to regions with endemic parasitic diseases.
12. Concomitant disease with abdominal symptoms likely to complicate the evaluation of IBS symptoms (e.g. painful menstrual disorders).

Screen Failure (Case and Controls)
1. Endoscopic examination showed evidence for organic gastrointestinal disease (abnormal gross appearance of the mucosal tissue and suspicious abnormalities identified).
2. Histopathological investigation of biopsy specimens showed evidence for collagenous or lymphocytic colitis based on standard diagnostic criteria.
3. Abnormal laboratory studies (e.g. chemistry, complete blood cell count) as those being above or below the 95th percentile for reference range).

Subject Recruitment and Consent Process
Case Identification

Cases were identified and initially screened to determine eligibility from the following sources: 1) Referrals to the department of gastroenterology with either a diagnosis of diarrhea and/or constipation and abdominal pain, and/or possible or probable diagnosis of IBS or for routine colon cancer screening, 2) after consultation with a gastroenterologist and referred for consideration for participation in this study and 3) reviewing weekly information systems (IS) reports by research coordinator (RC) of all new patients referred for suspected IBS or symptoms of chronic diarrhea with or without abdominal pain to Gastroenterology Departments. Prescreening inclusion/exclusion criteria was initially applied to patients to determine potential eligibility. For case consideration subjects had to meet all of the criteria listed in the inclusion/exclusion criteria. Patients with a previous IBS diagnosis on medications specifically to treat their IBS symptoms [antispasmodics (dicyclomine (Bemote, Bentyl, Do-Spaz) and hysocyamine (Levisin, Levbid, NuLev), antidiarrheal (loperamide (Imodium, a kaolin/pectin preparation (Kaopectate, and diphenoxy late/atropine (Lomotil), antidepressants (Imipramine (Tofranil), amytriptyline (Elavil), nortriptyline (Pamelor, and desipramine (Norpramin), or Alosetron (Lotrenox)] were required to stop these medications for at least 1 weeks prior to enrollment. Patients on probiotics were required to stop these medications for at least 2 weeks prior to enrollment.

Phase 1: Study Procedures
Screening for Eligibility

Cases were identified and initially screened to determine eligibility from the following sources: 1) Referrals to the department of gastroenterology with either a diagnosis of diarrhea and/or constipation and abdominal pain, and/or possible or probable diagnosis of IBS, 2) after consultation with a gastroenterologist and referred for consideration for participation in this study and 3) reviewing weekly information systems (IS) reports by research coordinator (RC) of all new patients referred for suspected IBS or symptoms of chronic diarrhea with or without abdominal pain. For case consideration subjects had to meet all of the criteria listed in the inclusion/exclusion criteria. Prescreening inclusion/exclusion criteria were initially applied to patients to determine potential eligibility by the RC.

Schedule of Measurements

Each consecutive patient case and control was evaluated by clinical history, complete blood cell count (CBC w/o diff), serum chemistry (comprehensive metabolic panel (CMP), quantitative serum immunoglobin levels-IGM only, gasar tissue transglutaminase antibodies-AB, IGA, IGG and erythrocyte sedimentation rate (ESR).

For these evaluations, two venous blood samples (one Lavender Top & one Red Top, approximately 10 cc each) of whole venous blood were collected. The Lavender Top-10 cc tube containing EDTA was centrifuged, processed for plasma and analyzed for CBC w/o diff and ESR. The Red Top-10 cc tube containing spray-coated silica and polymer gel was centrifuged, processed for serum and analyzed for quantitative serum immunoglobin, serum chemistry and tissue transglutaminase antibodies. Samples were collected and shipped to Marshfield Laboratories or Marshfield Clinic Research Foundation Core Laboratory for processing.

Clinically significant abnormalities in any of the test results lead to study exclusion. Based on the Rome III criteria, cases were subdivided into two subgroups (diarrhea, mixed) according to the stool form as assessed by the Bristol Stool Form (BSF) scale. The BSF describes the stool into 7 categories based on the appearance were 1-2, separate 1, hard lumps like nuts (difficult to pass) from 2; sausage shaped but lumpy) and 6-7 were 6, fluffy pieces with ragged edges, a mushy stool and 7, watery, no solid pieces, entirely liquid.

Information obtained included the following:
Family history of IBS in parents, siblings or children
Abdominal bloating or distension
Incomplete evacuation
Straining with defecation
Fecal urgency
Mucus in the stools
Abdominal pain, discomfort or cramping
Symptoms improved with defecation
Diarrhea-predominant subtype of IBS (IBS-D) characterized by loose (mushy) or watery stools** on at least 25% of the bowel movements and hard or lumpy stool* <25% of bowel movements
Mixed subtype of IBS with the presence of both hard or lumpy stools* and loose (mushy) or watery stools** occurring, in each case, on at least 25% of the bowel movements
* Bristol Stool Form Scale 1-2
** Bristol Stool Form Scale 6-7

The clinical severity of IBS symptoms was assessed in cases by using the Francis Severity IBS score and IBS quality-of-life (QOL) score during the initial symptomatic (active) and asymptomatic (symptom remission visits). The IBS severity score consist of 5 questions measuring the severity and frequency of abdominal pain and associated symptoms. Each question is given a value measured on a scale from 0 (no symptoms) to 100 (most severe symptoms) with a maximum possible score of 500. The sum of the score from each question is considered the severity score. The IBS QOL questionnaire consists of 34 questions which ask patients to think about their lives over the past 30 days when determining their responses. Each question is rated on a Likert scale from 1 (not at all) to 5 (extremely, a great deal). The sum of the score from each question is the total QOL score. The Francis Severity IBS score and IBS QOL will be used to assess whether an association exists between severity of IBS symptoms and pattern of gene expressed.

Colonoscopic procedures were performed as recommended by a gastroenterologist experienced in optical colonoscopy using standard equipment. Two mucosal tissue samples were obtained for case and control subjects by endoscopy from adjacent sites at the sigmoid colon 20-30 cm measured during withdrawal. Upon collection, 1 colonic mucosal biopsy tissue sample were placed into a transport vial containing an RNA stabilization media. The sample was shipped at room temperature to Marshfield Clinic Research Foundation-Core Laboratory, logged in and stored at −80° C. Samples were batched for later overnight shipment on dry ice to Todd Sandrin's laboratory at the Arizona State University and stored at −80° C. until analyzed. The second sample was sent for histopathological examination to the department of pathology and evaluated according to standard processing procedures.

Data Collection

The following data points were recorded for all subjects (cases and controls):
Date of Birth
Gender
Race
Concomitant medications
Date of colonoscopy
Histopathological results of colon biopsy Results of laboratory studies [complete blood cell count (CBC w/o diff), serum chemistry comprehensive metabolic panel (CMP), quantitative serum immunoglobin levels-IGM only, gasar tissue transglutaminase antibodies-AB, IGA, IGG and erythrocyte sedimentation rate (ESR)]

Confirmation of recent travel to regions with endemic parasitic diseases

The following additional data points were recorded for all cases:

Verification of IBS diagnosis according to Rome III criteria
Stool form assessment by the Bristol Stool Form (BSF) scale
Clinical severity of IBS symptoms as assessed by the Francis Severity IBS score
IBS quality-of-life (QOL) score
Phase 2: Study Procedures From the same 16 cases and controls, we also collected blood and stool samples for further investigation (beyond the scope of the work proposed here) for potential DNA (to be obtained from blood samples), protein (to be obtained from blood, fecal and the same mucosal tissue samples from which RNA will be harvested), and microbial (by analyzing microbial populations from fecal samples) biomarkers. Blood and stool samples were stored at Arizona State University until funding is available to complete studies on these specimens. Collection of these additional samples at the same time as the tissue sample is collected provides composite information about potential interactions between the intestinal microbiome and expression of other blood biomarkers in IBS patients during periods of active disease and during an asymptomatic period.

Blood Sample

In total, three venous blood samples (one Lavender Top & Two Red Tops, approximately 10 cc each) of whole venous blood was collected for this future DNA and protein analysis. The Lavender Top-10 cc tube containing EDTA will be frozen immediately and stored at −80° C. for DNA analysis. The two Red Top-10 cc tubes containing spray-coated silica and polymer gel will be centrifuged and processed for serum. Serum aliquots (approximately 4 cc) will be frozen and stored at −80° C. for protein analysis. All samples will be frozen/processed at each participating site of collection, shipped overnight on dry ice to Marshfield Clinic Research Foundation-Core Laboratory, recorded and stored at −80° C. Samples will be batched for later overnight shipment on dry ice to Todd Sandrin's laboratory at the Arizona State University and stored at −80° C. until analyzed.

Stool Sample

The following directions were given to participants for the purpose of the self-collected stool samples from the period of initial enrollment visit until colonoscopy preparation:

Note: Upon receiving the stool collection kit, please freeze gel packs.

1. Please wash your hands before beginning the procedure.
2. DO NOT pass the specimen into the toilet.
3. DO NOT pass the specimen directly into the collection vial. Pass the stool specimen onto the dry pan provided. Carefully open each vial. Using the spoon attached to the cap, collect small amounts of stool from areas that are slimy, watery, or bloody and place them into each vial up to the FILL LINE located on the label.
4. If the stool is hard, collect small amounts from both ends and the middle and place into each vial.
5. DO NOT urinate on the specimen or into the collection vial.
6. DO NOT allow any water to mix with the specimen.
7. KEEP STOOL SAMPLE FROZEN AT ALL TIMES. Return stool sample, ON FROZEN GEL PACKS, to the closest participating institution.

Fecal samples (approximately 10 grams) were self-collected using a stool collection kit provided to each site by Marshfield Clinic Research Foundation (MCRF)-Core Laboratory. Subjects were instructed to freeze sample immediately and transport on frozen gel packs to their participating research site. Samples after brought to their research site were shipped on dry ice to MCRF-Core Laboratory. MCRF-Core laboratory recorded and stored samples at −80° C., and batched for later overnight shipment on dry ice to Todd Sandrin's laboratory at the Arizona State University. Samples were stored at −80° C. for analysis detailed below.

IBS Patients (Cases)

Fecal samples were collected at the time of initial symptomatic (active disease) presentation prior to colonoscopy. Fecal samples were also obtained during an asymptomatic period defined as a 2 week period without IBS symptoms at least 4 week post-colonoscopy.

Control Patients

Fecal samples were obtained prior to a scheduled routine colonoscopy examination.

A. DNA:

DNA was isolated from ten milliliters of whole blood using the PUREGENE DNA purification kit purchased from Gentra Systems (Minneapolis, Minn.). In this procedure, blood is collected in EDTA tubes to reduce DNA degradation. Red blood cells are lysed and white blood cells are collected by centrifugation. White blood cells are then lysed and proteins are precipitated. The collected supernatant containing the DNA is precipitated using isopropanol and collected by centrifugation. Following rinsing of the pellet with 70% ethanol, the DNA is resuspended in buffer and stably stored indefinitely at −20 degrees C. The yield from 10 ml blood is about 150-500 µg DNA.

B. Proteins:

Stool and serum samples were initially analyzed directly (no protein purification) using matrix-assisted laser desorption ionization time-of-flight (MALDI-TOF) mass spectrometry as described below. Acetone precipitated proteins from each sample were also analyzed. If abundant serum proteins interfered with this analysis, we used affinity chromatography (Multiple Affinity Removal Hu-14 Columns; Agilent Technologies) to reduce levels of interfering proteins prior to MS analysis. We also isolated total protein from the same tissue samples from which we isolated RNA.

Stool samples (described above) were used to construct 16S rRNA gene libraries as described in additional detail below. Total DNA was extracted from 125 mg of each of the fecal samples using the Qiagen DNA Stool Mini kit (Qiagen; Valencia, Calif.) prior to PCR and subsequent analysis described in more detail below.

Visit 1

Initial enrollment visit (Study visit 1): informed consent, blood (50 cc total) samples, stool collection instructions, and study-related procedures. Subjects consented using a current informed consent form that was approved by the respective study site's Institutional Review Board. Subjects were allowed adequate time to read the informed consent, discuss the consent with study staff and others (e.g., family members, friends, or any of their health care providers), and have their questions answered prior to signing the informed consent.

After informed consent was obtained, demographic information, laboratory tests, Francis Severity IBS score and IBS quality-of-life (QOL) score were obtained. Subjects were asked to provide a stool (fecal) sample prior to the colonoscopy preparation. Subjects were given a pre-labeled container and instructions for storage and shipping.

Visit 2

Procedural visits (Study visit 2): tissue mucosal biopsies were obtained.

Sample Procurement

All mucosal tissue samples were obtained from subjects as described by Costello et al. (2005). Briefly, a sample was obtained from the sigmoid colon (at 25 cm measured from withdrawal), placed into a transport vial containing an RNA stabilization media, shipped by each participating site at room temperature to Marshfield Clinic Research Foundation-Core Laboratory, recorded and stored at −80° C. Samples were batched for later overnight shipment on dry ice to Todd Sandrin's laboratory at the Arizona State University and stored at −80° C. until further analysis. RNA was extracted from a subsample of the tissue as described below.

Laboratory Analysis

Microarray Analysis

We initially isolated RNA from mucosal tissue samples from 10 normal controls and 10 IBS cases as described in the protocols section of this document. RNA isolation was performed by personnel in Dr. Jurutka's laboratory at Arizona State University with recent and extensive experience in this area. Per Nimblegen (Nimblegen Systems Inc., Madison, Wis.)-specified protocols, RNA quality was verified spectrophotometrically. An aliquot of each RNA extraction was stored at −80° C. for further qPCR analysis as described below. cDNA was synthesized and a clean-up step was performed to remove residual RNA using RNase. cDNA samples was sent on dry ice via overnight courier to Nimblegen. Nimblegen personnel performed the hybridization of cDNA to the microarrays as described in the protocols section of this document. Briefly, cDNA was precipitated with ethanol and dried in a SPEEDVAC. DNA quality was verified spectrophotometrically, labeled with Cy3, and hybridized to Nimblegen ultra high-density oligonucleotide arrays containing 385,000 features. The ultra-high density design of Nimblegen arrays makes them advantageous over other microarray platforms for the following reasons: 1) the effect of inconsistent probe behavior is minimized, 2) signal-to-noise ratios tend to be higher on microarrays containing more probes per gene, and 3) the long oligonucleotides (60 mers) increase accuracy (Nimblegen, 2007).

Differentially expressed genes were identified using proprietary Nimblegen software (NimbleScan). The software employs the Robust Multi-Array Analysis (RMA) algorithm. This statistical approach has been shown to increase reproducibility and sensitivity of high-density oligonucleotide microarray data such as that generated in this study. The software's use of RMA also allows quantile normalization and background correction of the microarray data. Data was further explored using ArrayS TAR software (DNAStar; Madison, Wis.). Specifically, the software was used to: i) construct scatter plots to compare expression of genes in case and control tissue samples and ii) to construct heat maps of gene expression patterns using hierarchical clustering (k-Means). To characterize gene functions and further synthesize the data (i.e., determine which genes are involved in which cellular processes), we obtained Gene Ontology (GO) terms for differentially expressed genes using tools available through the Gene Ontology Project.

Validation of Differentially Expressed Genes Through qPCR

Quantitative PCR (qPCR) was used to validate and more thoroughly characterize differential expression of 10 candidate biomarker genes in a larger pool of patients. The 10 genes exhibiting the most significant differences in expression between case and control tissue samples composed this set of 10 candidate biomarker genes. Genes that were nonspecifically expressed, including inflammatory markers, were identified by examining the sequence homologies of each potential candidate biomarker gene with those in publicly available databases (e.g., NCBI BLAST). Candidate biomarker genes displaying >95% homology to genes known to be involved in nonspecific, inflammatory responses will not be included in any further analysis. In addition to the initial 10 normal controls and 10 IBS cases used above, 15 additional normal control and 15 additional IBS case samples will be used. qPCR will be employed on all 50 samples (25 normal controls and 25 IBS cases) to validate and quantify the extent of differential gene expression detected with the microarray approach described above. Transcripts will be quantified using the TaqMan PCR approach (Applied Biosystems; FosterCity, Calif.), because of its superior specificity compared to SYBR Green-dependent approaches. Primers for each of the 10 candidate biomarker genes will be designed to target non-redundant sequences using Primer Express 2.0 (Applied Biosystems). Total RNA (1 µg) obtained as described above will be reverse transcribed to cDNA using MultiScribe Reverse Transcriptase (Applied Biosystems). An MJ Opticon (MJ Research; Waltham, Mass.) real-time thermal cycler housed at the Arizona State University will be used to perform PCR reactions and to detect relative transcript levels. β-actin will be used as the endogenous control.

Differences between candidate biomarker expression levels in normal control and IBS case samples will be evaluated using Mann-Whitney U tests, and p-values less than 0.05 will be deemed significant.

Visit 3 (Unscheduled)

Asymptomatic (unscheduled) visit cases only: stool specimen will be obtained using the procedure described in Visit 1 and Francis Severity IBS score and IBS Quality of Life questionnaires will be completed and mailed.

Rescue Medication

Patients will be required to stay off all medications used for the treatment of IBS throughout the study period. Patients whose diarrhea is intolerable will be allowed to take Imodium 2 tablets every 6 hours as needed.

Phase 2 Studies

Whole Genome Scan

DNA was obtained and used for research initiatives that applied DNA microarray techniques for whole genome scanning in order to identify genetic variability and other genetic markers found in patients with IBS.

Protein Biomarkers

Given the large number of genes with expression patterns associated with gastroenterological disorders, it is reasonable to assume that certain gene products (i.e., proteins) might also be differentially expressed in patients with IBS in comparison to controls (i.e. those with an absence of gastrointestinal symptoms and who are scheduled to undergo colonoscopy for routine colon cancer surveillance with endoscopic and histological examination yielding no significant pathological findings). As with the genetic data, the literature contains little data regarding biomarkers for IBS. There is mounting evidence that fecal calprotectin may be a useful biomarker of IBD. Median stool calprotectin concentrations in healthy adults ranged from 9.3 µg/g to 58 µg/g, but from 62 µg/g to 1,722 µg/g in adults with IBD. Calprotectin is a highly stable glycoprotein present in leukocytes that has emerged as a potentially useful test for inflammation of the intestinal wall. Fecal calprotectin lacks sufficient specificity to be used exclusively as a biomarker in diagnosis of IBD. While fecal calprotectin has not been reported to be useful in diagnosing IBS, fecal serine protease activity may have promise as an IBS biomarker. Serine protease activity was higher in patients with IBS than in healthy patients (64 U/mg vs. 25 U/mg). The increased activity was not due to mucosal inflammation, suggesting that the increased fecal serine protease originated from intestinal microflora. We rapidly screened stool, serum, and tissue protein samples for candidate IBS markers using Matrix-Assisted Laser Desorption Ionization Time-of-Flight (MALDI-TOF) Mass Spectrometry (MS) and subjected the same samples to more rigorous, albeit more time-consuming, screening using liquid chromatography (LC) MS/MS.

Samples were initially analyzed directly (no additional protein purification) using matrix-assisted laser desorption ionization time-of-flight (MALDI-TOF) mass spectrometry. Acetone precipitated proteins from each sample will also be analyzed. If abundant serum proteins interfered with this analysis, we used affinity chromatography (Multiple Affinity Removal Hu-14 Columns; Agilent Technologies) to reduce levels of interfering proteins prior to MS analysis. For all intact samples and precipitated proteins, we scanned multiple mass ranges (e.g., 400 Da-4,000 Da and 3,000 Da-20,000 Da) in our search for masses unique to particular samples as we have described recently. Post-source decay (PSD) will be used when appropriate (i.e., with candidate biomarkers with masses ranging from 400 Da to 3,500 Da) for additional characterization and identification of candidate biomarkers. While less rapid, we anticipate that LC-MS/MS analysis will allow identification of a greater number of proteins in each sample than MALDI-TOF. For this analysis, acetone precipitated proteins from stool and affinity chromatography-purified proteins from serum samples will be used. If candidate protein biomarkers are found with LC-MS/MS but not with our initial MALDI-TOF screen, we will explore development of rapid sample preparation procedures to allow the more rapid MALDI-TOF analysis to be used to detect the candidate biomarker detected by LC-MS/MS. For LC-MS/MS analysis, sample preparation will be performed according to a protocol established by the Biotechnology Center, University of Wisconsin Madison. Protein samples will be digested with 20 ng/ml trypsin in 25 mM (NH4) HCO3 at 41° C. and placed into clean 0.65 ml siliconized EPPENDORF tubes. Peptides will be obtained from solution by drying in a vacuum centrifuge for ca. 1.5 h. The peptides will be desalted using C18 ZipTips according to manufacturer's protocols using appropriate acids (e.g. formic acid) to prevent ion pairing during ionization. Peptides will be stored at −80° C. until LC-MS/MS analysis. Peptides will be separated using an Agilent 1100 HPLC system with nano-pump flow capability coupled to an Agilent MSD ion trap mass spectrometer. Samples will be initially separated on a ZORBAX C-18sb trap column at 0.280 ml/min for 15 min. The trap column will be eluted to a 75 mm×150 mm analytical column in a 120 min gradient from 0.1% FA/10% ACN/water to 0.1% FA/60% ACN/water. Over the course of 10 min, the ACN will be ramped up to 95%. Afterwards, the column will be re-equilibrated with 10% ACN for 20 min. Peptides will be eluted from the analytical column directly into the ion trap via an 8 mm glass spray needle. The ion trap will be configured to prefer doubly charged ions and trigger MS/MS at 0.1% of the absolute maximum intensity as a threshold value. Peptide fragments in each cycle will be resolved using Agilent proprietary software for the ion trap. Mass spectrometer data will be converted to .mgf files using the Agilent ion trap software and searched against the human portion of the National Center for Biotechnology Information (NCBI) database using MASCOT (Matrix Science; Boston, Mass.). Hits with a Mowse score >40 will be collected.

Microbiota

Emerging evidence suggests that the intestinal microbial milieu may play a role in IBS and that modification of the intestinal microflora through feeding probiotics may result in symptomatic improvement. Quantitative and qualitative changes in the resident intestinal microbiota may play a role in or are a result of altered motility in patients with IBS. The mechanism by which intestinal microbiota modulate intestinal inflammation leading to IBS symptoms is incompletely understood. A possible microbial cause of IBS has been postulated for decades, but a specific group of causative microorganisms has yet to be determined. Even the presence of particular groups of microorganisms that correlate with IBS has not been completely described. Furthermore, it is unknown whether the intestinal microbiota changes during symptom free-periods of disease.

There have been many reports of different microbial communities in patients with IBS compared to healthy controls, but many of these studies have focused on culturable microorganisms. Unfortunately, the majority of intestinal microorganisms are resistant to traditional cultivation techniques. Relatively recent advances in molecular microbial ecology have allowed investigation of complex communities of microorganisms, regardless of whether they are culturable or not.

Additionally, potential biomarkers of IBS likely exist and we concede that the design of new real-time PCR assays would be required to more fully analyze the intestinal microflora of patients with IBS. Focusing on clostridial groups and using denaturing gradient gel electrophoresis (DGGE), some have reported microbial population instability in patients with IBS. While results of these recent studies have proved enlightening, they have been limited by the approaches they employed. Real-time PCR can only detect groups of microorganisms for which primers have been optimized. DGGE-based studies, particularly those targeted to selected clostridial groups, may underrepresent diversity. Thus, it is reasonable to assume that a host of additional microbial population differences exist between the intestines of patients with IBS and healthy individuals and may readily be exploited as biomarkers for IBS.

We constructed 16S rRNA gene libraries using fecal samples of patients and healthy controls to identify microorganisms that may be used as biomarkers of IBS. To construct the libraries, total DNA was extracted from 125 mg of each of the fecal samples using the QIAGEN DNA Stool Mini kit (QIAGEN; Valencia, Calif.). PCR was performed on the extracted DNA to amplify 16S rRNA-encoding genes within each sample using appropriate forward (S-*Eub-0339-a-A-20: 5'-CTC CTA CGG GAG GCA GCA GT-3') (SEQ ID NO. 1) and reverse (S*-Univ-1385-b-A-18: 5'-GCG GTG TGT ACA AGR CCC-3') (SEQ ID NO. 2) primers. Amplification was performed as described by Mangin et al. (2004). Cloning of PCR products was performed using the Topo TA Cloning Kit for Sequencing (Version N, Invitrogen Life Technologies, Carlsbad, Calif.) and One Shot® Mach 1™ TIR Chemically Competent *E. coli* cells (Invitrogen Co., Carlsbad, Calif.). Approximately 100 randomly selected clones will be sequenced. Inserts will be PCR amplified using M13 primers, and products will be sequenced using an ABI 3730 xl DNA sequencer which utilizes the Sanger dideoxy-chain termination method for DNA sequencing. Sequences will be characterized using the Basic Local Alignment Search Tool (BLAST) and aligned using Vector NTI Advance™ 10 sequence analysis software (Invitrogen Corporation, Carlsbad, Calif.). Sequences of less than 300 bp and chimeric sequences (as detected by the RDP CHECK_CHIMERA program) will be removed from the analysis. ClustalW and NJ Plot software will be used to create dendrograms to visualize the relatedness of sequences. Bootstrap values of 1000 will be used in the construction of the dendrograms. In subsequent work, we design real-time PCR assays to quantify candidate biomarker microorganisms in these and additional case samples and healthy controls.

Working Example 2

Regarding experiments completed, we have isolated RNA from human colonic tissue samples. The RNA was converted to cDNA, fluorescently labeled and hybridized to DNA microarrays representing the entire human genome (8-plex Agilent microarrays). We have done this for 16 samples (8 controls and 8 IBS patients, in Working Example 1). We also have performed another DNA hybridization with another 8 samples (5 controls and 3 IBS patients, in Working Example 2), bringing the total number of samples to 24. The cDNA synthesis, microarray hybridization, and scanning of the arrays were performed by Ambry Genetics (who we contracted for this service found online). The array data we received from Ambry Genetics was analyzed using common microarray analysis software (ArrayStar by DNAStar; Madison, Wis.). Data were statistically analyzed using built-in functions of the ArrayStar software found online.

Laboratory Equipment Needed

−80 C freezer, −20 C freezer, 4 C refrigerator, 37 C water bath, centrifuge, vortex mixer, spectrophotometer, microcentrifuge, pipettors, pipette aid, biological safety cabinet; equipment for microarray hybridization detailed in attachment (Nimblegen microarray hybridization protocol.pdf).

Laboratory Supplies Needed

Pasteur pipettes, sterile pipets, conical tubes, Aurum Total RNA Mini Kit (BioRad Cat#732-6820), pipette tips with filter, TE buffer, liquid nitrogen, microfuge tubes, 95-100% ethanol, β-mercaptoethanol (BioRad Cat#161-0710), 10 mM Tris, pH 7.5 with RNase free water, 70% ethanol, Kontes 0.5 mL pellet pestle microfuge tubes (Fisher Cat# K749510-1590).

Specific Handling Procedures

Outline:
1) Obtained tissue sample from patient
2) Prepared RNase-free tissue lysate
3) Isolated total RNA
4) Performed reverse transcriptase reaction (cDNA synthesis) using the RNA sample (see separate cDNA synthesis protocol)
5) Hybridized cDNA to microarrays (Nimblegen)

Preparation of Lysate from Tissue Sample:

Washed hands well before setting up area.

Wiped down surface of hood with 70% ethanol. All steps were performed in an RNase-free environment; take proper RNase-free precautions.

Labeled each 0.5 mL "micro pestle" tube for each tissue sample.

Added small quantity of liquid nitrogen to frozen tissue sample (enough to just cover tissue). Grinded tissue in micro pestle tube in liquid nitrogen until a fine powder is obtained. Allowed liquid nitrogen to evaporate.

Added 350 µL of lysis solution (already supplemented with 1% β-mercaptoethanol) to each tube containing the homogenized tissue. Pipetted up and down at least 20 times or until the solution is homogeneous. It is very important to obtain a completely homogenized lysate in order to obtain high quality RNA. Checked that the tissue lysate did not contain unlysed cells under the microscope.

Total RNA Isolation:

RNA Isolation:

Added 350 µL of 70% ethanol to each tube of completely homogenize tissue lysate (from above step). Pipetted up and down 15 times to mix thoroughly.

Ensured that the solution is homogeneous and the viscosity is reduced.

Placed an aliquot of elution solution (from kit) in an RNase free microfuge tube and placed tube into a 70 C heat block. Each sample required 80 µL of elution solution; made sure to have a little extra (n+1) warmed up to account for pipetting errors.

Inserted RNA binding columns into 2 mL capless wash tubes (provided with the kit).

Pipetted the homogenized tissue lysate into the RNA binding column. Centrifuged for 1 min. Discarded the filtrate from the wash tube and replace the binding column into the same wash tube. If some of the lysate did not go through the column, centrifuged longer (this sometimes indicates either incomplete lysis or too much tissue).

Added 700 µL of low stringency wash solution to the RNA binding column.

Centrifuged for 1 min. Discarded the filtrate and replaced the column(s) into their respective wash tubes.

Thawed out enough of reconstituted DNase (from kit) to obtain 5 µL per sample. For each column mixed 5 µL of DNase solution with 75 µL of DNase dilution solution.

Added 80 µL of diluted DNase to each column. Incubate columns with DNase for 15-20 min, then centrifuge the columns for 30 seconds and discard the filtrate.

Added 700 µL of high stringency wash solution to each RNA binding column.

Centrifuged for 30 seconds. Discarded the filtrate, replace columns into the collection tubes.

Added 700 µL of low stringency wash solution to each RNA binding column.

Centrifuged for 1 min. Discarded the flow-through.

Centrifuged for additional 2 min to remove residual wash solution. Discarded residual filtrate and the 2 ml tubes after this step.

Transferred the RNA binding columns to a new 1.5 mL labeled, capped microcentrifuge tubes (provided).

Pipetted 80 μL of warmed elution solution (from 70 C heat block) directly onto membrane stacks of the RNA binding columns. Incubate for 1 min. Centrifuged for 2 min. Discarded FILTER, not filtrate, and stored on ice while prepping to quantitate the RNA on the spectrophotometer. Quantitated RNA using a spectrophotometer. The 260/280 ratio is usually between 1.9 and 2.2. Each sample was measured twice using dilutions, such as 2 μL of RNA into 98 μL of TE, to ensure accurate quantitation. If the ratio was too low the sample was contaminated with protein and may not be suitable for downstream applications.

Aliquoted the RNA into 2 μg per tube portions, labelled them clearly, and stored at −80 C. Each of the RNA samples were reverse-transcribed to produce cDNA used in the microarray.

For each reverse transcriptase reaction the following was mixed in a thin-walled 0.2 mL PCR tube:
X volume of RNA containing 2 mg of RNA
2 mL of iScript enzyme mix containing reverse transcriptase
8 mL of buffer solution
add ultra-pure H2O for the total reaction volume of 40 mL
use the following thermal cycler regime for the reverse transcription:
Shipping Instructions:

After completion of cDNA synthesis, samples were frozen at −20 C. Samples were shipped overnight on dry ice. cDNA samples were shipped on dry ice via overnight courier to Nimblegen.

Microarray Hybridization:

Microarray hybridization was performed by Nimblegen personnel using the protocol appended to this proposal (Nimblegen microarray hybridization protocol.pdf).

TABLE 2

Sample Description

| First Data Set | | Second Data Sat | |
|---|---|---|---|
| Sample Name | Type | Sample Name | Type |
| IBS-002 | Case | IBS-009 | Case |
| IBS-003 | Case | IBS-013 | Case |
| IBS-004 | Case | IBS-022 | Control |
| IBS-006 | Control | IBS-024 | Case |
| IBS-007 | Case | IBS-025 | Case |
| IBS-010 | Control | IBS-026 | Control |
| IBS-012 | Control | IBS-027 | Control |
| IBS-016 | Control | IBS-056 | Control |

TABLE 3

| SurePrint G3 Human GE v2 8 × 60k Microarray | |
|---|---|
| Design ID | 033434 (Agilent) |
| Species | *Homo Sapiens* (Human) |
| Format | 8 × 60K |
| Biological Features | 50,599 probes (~60 mer each) |
| Feature Layout | Randomized |
| Replicates of Biological Probes | 900 × 10 |
| RefSeq genes targeted | 24,588 |
| Positive Controls | 96 × 10 ERCC control probes |
| | 10 × 32 Agilent control probes |
| Design based on | RefSeq Build 50 |
| | Ensemble Release 52 |
| | Unigene Build 216 |
| | GeneBank (April 2009) |
| | Broad Institute Human lincRNA catalog (November 2011) |
| | Broad institute TUCP transcripts catalog (November 2011) |

The following claims are not intended to be limited to the embodiments and examples described herein.

What is claimed is:

1. A method of detecting and treating Irritable Bowel Syndrome (IBS), comprising:

obtaining a colon tissue sample of a human patient;

measuring the level of KRTAP16-1, SNX10, EPHA3, and FLT4 mRNA in said colon tissue sample;

detecting that said human patient has IBS when the levels of KRTAP16-1, SNX10, and EPHA3 mRNA in said colon tissue sample are under expressed in comparison to the levels of KRTAP16-1, SNX10, and EPHA3 mRNA in a control colon tissue sample obtained from a human patient without IBS and the level of FLT4 mRNA in said colon tissue sample is over expressed in comparison to the level of FLT4 mRNA in a control colon tissue sample obtained from a human patient without IBS; and treating said human patient detected to have IBS with an IBS medication selected from the group consisting of dicyclomine, hysocvamine, loperamide, diphenoxylate/atropine, amytriptyline, nortriptyline, desipramine or alosetron.

2. The method of claim 1, wherein said IBS medication comprises dicyclomine.

3. The method of claim 1, wherein said IBS medication comprises hysocyamine.

4. The method of claim 1, wherein said IBS medication comprises loperamide.

5. The method of claim 1, wherein said IBS medication comprises diphenoxylate/atropine.

6. The method of claim 1, wherein said IBS medication comprises amitriptyline.

7. The method of claim 1, wherein said IBS medication comprises nortriptyline.

8. The method of claim 1, wherein said IBS medication comprises desipramine or alosetron.

* * * * *